United States Patent [19]

Efimov et al.

[11] Patent Number: 4,598,081
[45] Date of Patent: Jul. 1, 1986

[54] 1,3-DIOXO-1H-BENZ(DE)ISOQUINOLINE-2(3H) BUTYRIC ACID, PHARMACOLOGICALLY ACCEPTABLE SALTS THEREOF AND COMPOSITIONS CONTAINING THE SAME FOR TREATMENT OF DIABETES MELLITUS COMPLICATIONS

[75] Inventors: Andrei S. Efimov; Igor M. Melnik; Jury V. Tkachuk; Nikolai D. Tronko; Elena K. Efimova; Irina G. Obrosova; Vadim M. Gordienko; Leonid A. Kaminsky; Vasily I. Staninets; Jury L. Zborovsky; Nikolai A. Mokhort; Lora M. Kirichek, all of Kiev, U.S.S.R.

[73] Assignees: Nauchno-Issledovatelsky Institut Endokrinologii I Obmena Veschestv; Nauchno-Issledovatelsky Institut Farmakologii I Toksikologii; Institut Organicheckoi Khimii, all of Kiev, U.S.S.R.

[21] Appl. No.: 767,054

[22] Filed: Aug. 19, 1985

Related U.S. Application Data

[63] Continuation of Ser. No. 660,253, Oct. 12, 1984, abandoned, which is a continuation of Ser. No. 419,447, Sep. 17, 1982, abandoned.

[51] Int. Cl.$^4$ .................... C07D 221/14; A61K 31/47
[52] U.S. Cl. ...................................... 514/296; 546/98; 514/866
[58] Field of Search ........................... 546/98; 514/296

[56] References Cited

U.S. PATENT DOCUMENTS 3,821,383  6/1974  Sestanj .................................. 540/98
4,118,495 10/1978  Lippman .............................. 546/98

OTHER PUBLICATIONS

Bianchi et al., Chem. Abs. 64, 19481(a) 1967.

*Primary Examiner*—Mark L. Berch
*Attorney, Agent, or Firm*—Burgess, Ryan & Wayne

[57] ABSTRACT

1,3-dioxo-1H-benz(de)isoquinoline-2(3H) butyric acid having the following structural formula

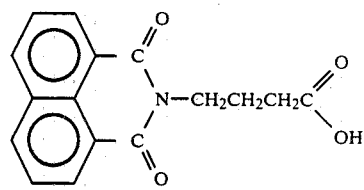

A pharmaceutical composition for treating diabetes mellitus complications comprises an active agent and a pharmaceutical base material, wherein the active agent is a compound selected from the group consisting of 1,3-dioxo-1H-benz(de)isoquinoline-2(3H) butyric acid, and the sodium and potassium salts thereof.

10 Claims, No Drawings

1,3-DIOXO-1H-BENZ(DE)ISOQUINOLINE-2(3H) BUTYRIC ACID, PHARMACOLOGICALLY ACCEPTABLE SALTS THEREOF AND COMPOSITIONS CONTAINING THE SAME FOR TREATMENT OF DIABETES MELLITUS COMPLICATIONS

This application is a continuation of application Ser. No. 660,253, filed Oct. 12, 1984, now abandoned, which is a continuation of application Ser. No. 419,447, filed Sept. 17, 1982, now abandoned.

FIELD OF THE INVENTION

The invention relates to 1,3-dioxo-1H-benz-(de)isoquinoline-2(3H)butyric acid, pharmacologically acceptable salts thereof, and compositions thereof. The invention can be used to treat diabetes mellitus complications.

SUMMARY OF THE INVENTION 1,3-dioxo-1H-benz(de)isoquinoline-2(3H)butyric acid has the following structural formula

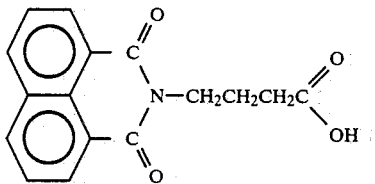

1,3-dioxo-1H-benz(de)isoquinoline-2(3H)butyric acid is a white fine-crystalline powder having a yellow tinge which is soluble in soda and alkali solutions, water-insoluble, and when heated is also soluble in alcohol and dimethyl-formamide.

The melting temperature of this butyric acid is 178° to 180° C. (from ethanol).

The sodium salt of 1,3-dioxo-1H-benz(de)isoquinoline-2(3H)butyric acid has the following structural formula

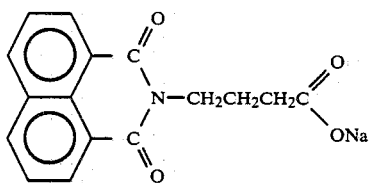

This sodium salt is a white powder having a yellow tinge which is readily soluble in water, slightly soluble in ethyl alcohol, and insoluble in benzole.

The melting temperature of said salt is 279° to 283° C. (accompanied by decomposition).

The potassium salt of 1,3-dioxo-1H-benz(de)isoquinoline-2(3H)butyric acid has the following structural formula

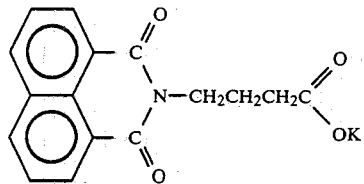

which potassium salt is a white powder having a cream tinge, readily soluble in water, soluble in ethyl alcohol, and insoluble in benzole. The melting temperature of this salt is 290° to 292° C. (accompanied by decomposition).

The invention is also concerned with a chemotherapeutic composition to treat diabetes mellitus complications, which composition according to the invention comprises 1,3-dioxo-1H-benz(de)isoquinoline-2(3H)butyric acid or pharmacologically acceptable salts thereof as an active agent, and a pharmaceutic base substance.

It has been established in recent years that metabolites of the sorbitol tract of glucose metabolism take part in the formation of diabetic angiopathy. The sorbitol tract of glucose metabolism includes two enzymes capable of converting glucose to fructose through sorbitol, aldose reductase and sorbitol dehydrogenase.

The glucose may penetrate into the cells of certain tissues (lenticular tissue, nervous tissue, kidney tissue, endothelium of vessels) without insulin. If the level of glucose in the blood increases, the endocellural concentration of said glucose also increases, the aldose reductase becomes more active, and the rate of conversion of the glucose to sorbitol also increases. The activity of the glucose metabolism sorbitol tract in the case of diabetes mellitus is 7 to 10 times higher. Since sorbitol does not readily penetrate through the cell membrane, it slowly accumulates between the cells. Under the action of sorbitol dehydrogenase the sorbitol is converted to fructose, but because the fructose is also metabolized only slightly in certain tissues, accumulation of sorbitol and fructose results inside the tissue causing retention of liquid and, as a result, tissue swelling. A high level of sorbitol and an osmotic disbalance may lead to swelling of the basilar membrane causing edema, hypoxia, disruption of the metabolic barrier of the vascular wall, and the formation of deposits of metabolites therein.

Accumulation of sorbitol in tissues may be decreased with the aid of the present composition.

It is desirable that the present composition treating diabetic complications include 1,3-dioxo-1H-benz-(de)isoquinoline-2(3H)butyric acid or pharmacologically acceptable salts thereof as an active agent, taken in the amount of 0.25 to 0.5 g, and a pharmaceutical base substance.

The above composition may be used for preventing and treating the following diabetic complications: diabetic angiopathy, polyneuropathy, nephropathy, encephalopathy, retinopathy, and diabetic cataracts.

The pharmaceutical base material is preferably a pharmaceutical made in the form of tablets. For instance, the following fillers are used as the pharmaceutical filler: gelatin, talcum, paraffin, starch, lactose, pectin, acetylcellulose, calcium stearate, magnesium stearate, and polyvinylpyrrolidone.

The tablets are administered perorally, the dosage being 50 to 100 mg per kg of body weight per day, for 30 days in each treatment period which is repeated 2-3 times in a year depending on the gravity of the illness.

It is recommended that the present composition for treating diabetic complications contain sodium or potassium salts of 1,3-dioxo-1H-benz(de)isoquinoline-2(3H)butyric acid as an active agent, and a base substance, all the ingredients taken in the following amounts, in weight %:

sodium or potassium salt of 1,3-dioxo-benz(de)isoquino-
line-2(3H)butyric acid: 1 to 10
pharmaceutic base substance: 90 to 99

Said drug composition may be used in the form of an ointment for use at night to treat diabetic retinopathy and diabetic cataract.

In this case the pharmaceutic filler serves as a pharmaceutic base substance shaped into tablets.

The pharmaceutic filler may be, for instance, a mixture of anhydrous lanolin and Vaseline in the proportion of 1:9.

A drug composition is also possible wherein the pharmaceutic filler serves as a base substance shaped in the form of a rectal suppository. The weight of each rectal suppositories is 1.4 to 4.0 g. Their use is recommended in the case of disturbace of intestinal absorption. As a pharmaceutic filler for said suppositories use may be made of cacao butter, vegetable and animal fat, hydrogenated fat, fused blend of fat with wax and spermaceti, resin-free ozocerite, hard paraffin, and the like.

It is desirable that the chemotherapeutic composition for treating diabetic complications include 1-2% water solution of the sodium or potassium salt of 1,3-dioxo-1H-benz(de)isoquinoline-2(3H)butyric acid.

This drug composition may be used in the form of eyedrops for local application to treat diabetic cataracts and retinopathy.

DETAILED DESCRIPTION OF THE INVENTION

The high toxicity of 1,3-dioxo-1H-benz(de)isoquinoline-2(3H)butyric acid was examined by way of experiments performed on various animals: white mice, rats, and dogs. Mature animals both male and female, weighting 18 to 22 g (white mice), 180 to 220 g (rats), 11 to 15 kg (dogs) were used for said experiments.

1,3-dioxo-1H-benz(de)isoquinoline-2(3H)butyric acid was administered perorally, i.e. in a manner which is supposed to be used for administration of the prepared drug in the medical practice. The drug was introduced in the form of a starch suspension through a gastric tube.

In determining the high toxicity of 1,3-dioxo-1H-benz(de)isoquinoline butyric acid for mice, rats, and dogs 10 different doses were used ranging from 1280 to 6000 mg per kg of body weight. Each dose being examined was tested on 5-6 animals. A total of, 51 mice, 36 rats, and 5 dogs were used in experiments which were performed to determine the high toxicity of 1,3-dioxo-1H-benz(de)isoquinoline-2(3H)butyric acid.

$LD_{50}$ determined by the Lichfield and Wilcoxon method, or the Van der Waerden method was used as an index of high toxicity. The animals were kept under observation for 5 days. The symptoms of the acute lethal poisoning by 1,3-dioxo-1H-benz(de)isoquinoline-2(3)butyric acid was characterized by flaccidity, hypodynamia, and lower respiration rhythm. Only a few animals showed a short-time initial excitation. 6-8 hours later the animals laid down on the side, their condition became comatose, followed by death. That is the animals died slowly, as a rule, during the first 24-26 hours.

The results of examining the high toxicity of 1,3-dioxo-1H-benz(de)isoquinoline-2(3H)butyric acid are given in Table 1.

TABLE 1

| Animal species 1 | Dosage 2 | Percentage* of animal death 3 | $LD_{50}$ (mm per kg) 4 |
|---|---|---|---|
| White mice | 1260 | — | |
| | 1500 | — | |
| | 2000 | — | |
| | 3500 | — | |
| | 3750 | 3/5 | 3700(2466 to 5550) |
| | 4000 | 2/5 | |
| | 4500 | 4/5 | |
| | 4750 | 5/5 | |
| | 5000 | 3/5 | |
| | 5250 | 5/5 | |
| Rats | 3000 | 0/5 | |
| | 3500 | 2/5 | |
| | 4000 | ½ | 4000(3030 to 5280) |
| | 4500 | 3/5 | |
| | 5000 | 4/7 | |
| | 5500 | 4/5 | |
| | 6000 | 5/5 | |
| Dogs | 5500 | 3/5 | 3800(2235 to 6450) |

*in numerator is the number of the animals which died;
in denominator is the number of the animals in the group.

As may be seen from the above table $LD_{50}$ of 1,3-dioxo-1H-benz(de)isoquinoline-2(3H)butyric acid for mice was 3700 (2466.0 to 5590) mg per kg of body weight.

Similar to these results are the indices of high toxicity of 1,3-dioxo-1H-benz(de)isoquinoline-2(3H)butyric acid for rats and dogs. Thus, $LD_{50}$ for rats is 4000 (3030 to 5280) mg per kg, and for dogs is 3800 (2235 to 6460).

A range of lethal concentrations was determined to characterize the danger of occurence of acute lethal poisoning. According to the results obtained the range of lethal concentrations of 1,3-dioxo-1H-benz(de)isoquinoline-2(3H)butyric acid is relatively wide and constitutes for mice 3.4; for rats 2.36; and for dogs 2.88, which indicates that there may develop compensatory reactions in the organism in response to the introduction of 1,3-dioxo-1H-benz(de)isoquinoline-2(3H)butyric acid in a wide range of doses.

The analysis of the high toxicity of 1,3-dioxo-1H-benz(de)isoquinoline-2(3H)butyric acid simultaneously introduced indicates that it is a substance with low-toxicity.

Chronic toxicity of 1,3-dioxo-1H-benz(de)isoquinoline-2(3H)butyric acid and the butyrates thereof also determined.

The experiments were performed on rats, rabbits, and dogs. 1,3-dioxo-1H-benz(de)isoquinoline-2(3)butyric acid was administered perorally in amounts of 50 and 100 mg per kg five times in a week during 6 months. It is to be noted that during said experimental period there were no lethal cases among the experimental animals because of administration of the drug.

As indices of influence of 1,3-dioxo-1H-benz(de)isoquinoline-2(3H)butyric acid on the organisms of the animals use was made of the weight of the animals, the composition of the peripheric blood (leukocytes, white blood cells, erythrocytes, hemoglobin), and the function of the cardiovascular and respiratory systems. In addition, the action of the proposed drug on the carbohydrate and uropoiesis functions of the liver was also examined.

The above indices were examined at the beginning of the experiment and then after 1, 2, 3, 4, 5, and 6 months.

At the end of the experiments there were carried out pathomorphological examinations of the lungs, heart, liver, kidneys, adrenal glands, spleen, lymph nodes, intestine, stomach, pancreas, and thyroid glands.

During said experiment no changes in animal behavior was observed. There were also no changes in the anthropological data of the experimental animals in comparison with the animals of the control group. The increase in the weight of the animals during 6 months On the basis of the results thus obtained it may be concluded that 1,3-dioxo-1H-benz(de)isoquinoline-2(3H)butyric acid taken in the above-mentioned so examined doses did not cause morphological lesions in many organs of the dogs, rabbits and rats which were examined (lungs, heart, adrenal gland, spleen, lymph nodes, stomach, pancreas and thyroid glands). At the same time slight lesions in the liver and kidneys were observed in some animals. However, said lesions might be caused in the liver by peroral administration of the drug and in the kidneys by the removal of said drug.

TABLE 2

| No. | Indices being examined | Statistical indices | Initial data | Time of observation after the start of treatment (months) | | | | | |
|---|---|---|---|---|---|---|---|---|---|
| | | | | 1 | 2 | 3 | 4 | 5 | 6 |
| 1 | 2 | 3 | 4 | 5 | 6 | 7 | 8 | 9 | |
| 1. | Weight, g | n | 10 | 10 | 10 | 10 | 10 | 10 | 10 |
| 2. | | M | 182.0 | 263.0 | 290.0 | 336.2 | 389.4 | 402.5 | 440.2 |
| 3. | | ±m | 5.65 | 3.60 | 5.0 | 8.7 | 9.9 | 22.2 | 11.8 |
| 4. | | % of var. | | +44.5 | +59.3 | +84.7 | +113.8 | +121.1 | +141.7 |
| 6. | Hemoglobin, g % | n | 10 | 10 | 10 | 10 | 10 | 10 | 10 |
| 7. | | M | 93.4 | 99.6 | 97.1 | 107.5 | 104.8 | 96.3 | 99.4 |
| 8. | | ±m | 1.95 | 1.00 | 2.00 | 15.1 | 12.2 | 3.6 | 1.4 |
| 9. | | % of var. | | +6.6 | +3.96 | +15.1 | +12.2 | +3.1 | +6.4 |
| 11. | Leukocytes | n | 10 | 10 | 10 | 10 | 10 | 10 | 10 |
| 12. | | M | 9345 | 12,300.4 | 11,394.4 | 16,225 | 11,179.2 | 13750 | 9.356.2 |
| 13. | | ±m | 1129.0 | 1232.0 | 1127.0 | 1736.0 | 707.1 | 1488.0 | 1240.0 |
| 14. | | % of var | | +31.6 | +21.9 | +75.9 | +19.6 | +47.1 | +0.1 |
| 16. | Erythrocyte | n | 10 | 10 | 10 | 10 | 10 | 10 | 10 |
| 17. | (thousands) | M | 4,700 | 4,895 | 5,043 | 4,916 | 5,078 | 4,991 | 5,135 |
| 18. | | ±m | 25.7 | 35.93 | 31.00 | 49.6 | 24.8 | 31.00 | 43.4 |
| 19. | | % of var | | 4.1 | 7.3 | +4.6 | +8.0 | +6.2 | +9.2 |
| 21. | Urea | M | 16.2 | 17.8 | 15.8 | 16.9 | 19.7 | 17.2 | 21.1 |
| 22. | | ±m | 0.9 | 0.53 | 1.3 | 1.2 | 1.2 | 0.63 | 0.54 |
| 23. | | | | | | +4.3 | +21.6 | +6.2 | +30.2 |
| 25. | Urea nitrogen | M | 7.55 | 8.29 | 7.37 | 7.87 | 9.18 | 8.01 | 9.83 |
| 26. | | ±m | 0.41 | 0.24 | 0.6 | 0.56 | 0.55 | 0.29 | 0.25 |
| 27. | | % of var. | | +9.8 | −2.38 | +0.3 | +21.6 | −6.09 | +30.2 |
| 29. | Residual nitrogen | M | 18.10 | 18.9 | 17.9 | 18.4 | 19.6 | 18.2 | 21.5 |
| 30 | | ±m | 1.3 | 1.78 | 1.92 | 1.56 | 1.94 | 1.84 | 3.4 |
| 31. | | % of var. | | +4.4 | −1.1 | +1.6 | +8.3 | +1.1 | +18.7 |
| 33. | Urea ratio | | 41.7 | 43.8 | 41.2 | 42.3 | 46.8 | 44.01 | 45.7 |

The following designations and abbreviations are used in the table: n = the number of the animals under observation; M = arithmetical mean of the indices; ±m = standard deviation; % of var. = percentage of variation; P = significance of the experiment results.

was 0.258 kg for rats and 0.7 kg for rabbits. Only the dogs showed a tendency for a slight decrease in their body weight.

Table 2 presents data in tabulated form on the composition of the peripheric blood and uropoiesis function of the liver of rats which received 1,3-dioxo-1H-benz(de)isoquinoline-2(3H)butyric acid during 6 months in a dose of 100 mg per kg of the weight of the animals.

Data presented in Table 2 indicate that application of 1,3-dioxo-1H-benz(de)isoquinoline-2(3H)butyric acid during 6 months did not lead to a change in the blood-formation function and the composition of the peripheric blood, as well as the urogenous function of the liver in the rats. Similar results were obtained in the case of administering 1,3-dioxo-1H-benz(de)isoquinoline-2(3H)butyric acid and salts thereof to other species of animals.

On completion of the experiment (six months) the experimental animals were killed: the dogs were killed with thiopental, the rabbits with aeroembolism, and the rats with diethyl ether. Thereafter, the lungs, heart, liver, kidneys, adrenal glands, spleen, lymph nodes, intestine, pancreas and thyroid gland of the killed animals were examined. The material thus obtained was fixed in formole. There were prepared paraffin sections which were then stained with hematoxylin and eosin.

Dissection of the animals showed no lesions.

The above lesions show that 1,3-dioxo-1H-benz(de)isoquinoline-2(3H)butyric acid produces a slight non-specific irritating action on the liver and kidneys. This is confirmed by an elevated vessel permeability in the renal glomerulus (in the dogs only) and a slight local lesion in the liver and kidneys of the rabbits and rats.

There were also examined the influence of 1,3-dioxo-1H-benz(de)isoquinoline-2(3H)butyric acid and its salts on the progress of diabetic angiopathies.

The experiments were conducted on Wistar rats (males) having a weight of 140 to 160 g. The diabetes was caused by a single-time hypodermic injection of alloxan ("Chemapol") in a dose of 150 mg per kg of body weight. The animals used for the experiment had a level of glucose above 300 mg % set after injection of alloxan, glucosuria and also polydipsia.

The glood glucose was determined by applying a glucoseoxidase method, cholesterine by e.s.r. (erythrocyte sedimentation rate) method, aldose reductase by the method of Hayman and Kinoshita, sorbitol by a sorbitol-dehydrogenase method.

Biomicroscopy of the conjunctiva was effected with the aid of a microscope fitted with a camera and a flash lamp.

With the purpose of examining lesions in the vessels of the microcirculation path, the muscle capillaries of the rear limbs of the rats of both the control and experimental groups were examined with the aid of an electron microscope after 6 and 12 months from the begining of the experiment, and also after injection during one month of 1,3-dioxo-1H-benz(de)isoquinoline-2(3H)butyric acid to the animals having a prolonged alloxan diabetes.

The material for the experiment (pieces of the muscular tissue) was fixed by osmium fixative by the Millonig method, dehydrated and placed into epon-812. Very thin sections were contrasted by uranyl acetate and lead citrate by the Reynolds method and then examined in an electron microscope JEM-100 with an accelerating voltage of 80 kV. The capillary sections were photographed with 8,000–5,000x magnification. The negatives were enlarged five times and the thickness of the basal membrane of the capillaries was determined by the Yodayken method in 10–12 points along the perimeter of 10–12 vessels of each animal. When determining the average value, the maximum thickness of the basal membrane in the case of a bevel section of the capillaries was not measured, and if the pericytes were present in the walls their value was excluded from the total thickness of the vascular wall. The measurement error was checked by photographing the test-object having 1154 lines in one millimeter at the same magnification of the microscope.

For histological examination pieces of the kidney, liver and miocardium were fixed in 10% neutral formaline dehydrated in alcohol, and the paraffin sections were stained with hematoxylin and eosin, and also by the Van-Gizon method.

It has been established as a result of the biochemical examination of the same animals before injection of the alloxan that their blood glucose was $108 \pm 4.1$ mg. %, fructose was $3.31 \pm 0.47$ mg %, and the cholesterin was $112 \pm 4.6$ mg %.

The vascular network of the same animals was not clearly defined, the main vessels were closer to the pupil region of the iris and smaller in size, they are straight and have a small number of small vessels therebetween. The arterioles and venules were convoluted to a minimum extent and were running almost in parallel.

Administration of the alloxan caused pronounced changes in the indices which were examined. The experimental animals had hyperglycemia $-346.7 \pm 30.5$ mg % ($<0.001$), the fructose content increased up to $12.3 \pm 2.57$ mg % ($<0.01$), cholesterin content increased, uncertain, ($p > 0.1$) up to $122 \pm 5.6$ mg %.

In the case of prolonged decompensated alloxan diabetes in the animals there appeared specific changes in the microvessels. The vascular pattern of the iris was clear-cut. The veins were convoluted in the form of loops and expanded to a great extent. All the vessels were inflated and had ampullaceous protrusions. There were some microaneurisms close to the pupil region of the iris and hemorrhage. The blood flow was slow. There were observed sections of thrombosis and stasis, and 75% of the animals had a rine cataract, generally, of both eyes.

As a result of histological examination of the internal organs of the rats with clear-cut indications of alloxan diabetes the following structural lesions were observed: the kidneys were not macroscopically changed and it was established using a microscope that the glomerulus decreased in size, with their capillaries narrowed and some of them adhered, or had varicose dilatation. The nuclei of the endothelium were hyperchromic. Drops of hyalin were found between some loops of the capillaries. The slit of the Bownan's capsule of the glomerulus were considerably increased and the capsule walls became thicker. Lymphocytic infiltrates were often found around the glomerulus. The epithelium of the convoluted tubules was at some places swollen, as a result of which the lumens in such tubules were contracted, and at some places, on the contrary, the epithelium was found to be thicker, the nuclei were highly hyperchromic and the lumens of the tubules enlarged. There also occured at some places destruction of the tubules. The epithelial cells were frequently found desquamated, with the nuclei thereof pyknotic or completely absent, and around said tubules were found masses of the lymphocytes, histiocytes and fibroblasts. In the lumens of the tubules were found hyaline casts. The lesions in the straight tubules were less pronounced. However, their epithelial cells became thicker and their nuclei were hyperchromic. Between the tubules were frequently found lymphocyte infiltrates. Attention is drawn to the fact that vessel walls were thicker, they were saturated with plasma, and the adventitial layer was expanded.

The hepatocytes in the liver were swollen, intertrabecula lumens were not evident, and the lobes of the trabecules were disrupted. Most of the hepatocytes had macrogranular protoplasm, and the granules were frequently concentrated in the form of large clumps at one of the cell poles. The nuclei were hyperchromic and at some places were not present. There were frequently found groups of cells which were in a necrosis state. The hepatocytes were frequently found to be markedly increased, and the protoplasm consisted of large vacuoles, and the hyperchromic nuclei forced to the periphery. There were found many dark cells, which were smaller in size, and of angular shape. The protoplasm was remarkedly oxyphilic and homogeneous, and the nuclei were hyperchromic.

The central veins were enlarged, and the triad vessels were found to have thickened walls and perivascular infiltrates. There were also triads around which was observed an increased number of the connecting fibers between which were found fibrocytes, histiocytes, lymphocytes and some individual plasma cells. The nuclei of Kupffer cells were more frequently swollen and enlarged, but there were also wrinkled cells having pyknotic nuclei.

The Glisson's capsule was somewhat enlarged and the number of fibrocytes therein was increased.

The fibers in the myocardium had illegible transverse striation. The sarcoplasm was homogeneous and at some places finely granular. The fiber nuclei were hyperchromic and the blood vessels were moderately plethoric. The endothelium nuclei of the vessels were found to be swollen.

The examination carried out with the aid of an electron microscope showed that in the capillaries of the skeleton muscles there were found endothelium hyperplasia, clearly-defined pinocytosis, the basal layer was friable and thicker, which shows that in the muscles of the limbs of the rats having alloxan diabetes after six months there appeared indications of a diabetic microangiopathy.

One of the earliest and constant indications of microangiopathy is thickening of the capillary basal layer, which makes it possible not only to determine a lesion but also to quantitively evaluate to what extent it manifests itself and, hence its phase.

Determining the average thickness of the basal membrane of the capillaries in the control and experimental animals showed that already after six months of the experiment the basal membrane in the rats having alloxan diabetes increased one and a half times (up to 90 nm, i.e. nanometers and in the control group said thickness was 55-60 nm), and after 12 months it increased 3 to 4 times (160-220 nm).

Thus, the examinations showed that in the case of prolonged alloxan diabetes the rats, based on evident dystrophic and destructive lesions of the internal organs, had indications of lesion of the microcirculatory channel, similar to those which are observed in diabetic human beings. Affection of the vessels was observed both through the electron microscope when examining muscles of the limbs, and also through a biomicroscopic examination of the iris.

The diabetic angiopathy model thus obtained was used for treating metabolic lesions caused in the case of diabetes mellitus by 1,3-dioxo-1H-benz(de)isoquinoline-2H butyric acid or the salts thereof.

1,3-dioxo-1H-benz(de)isoquinoline-2(3H)butyric acid or the sodium or potassium salts thereof was administered to the experimental animals in the form of a starch suspension through a gastric tube, for period of 30 days, with the dossage being 50 mg per kg of body weight per day.

The animals were then killed and as a result of histological examination it was established that they had a marked therapeutic effect due to application of 1,3-dioxo-1H-benz(de)isoquinoline-2(3H)butyric acid.

The renal glomerulus became more plethoric, the epithelium of the tubules had a more clearly defined boundary, and the protoplasm became less vacuolized and granular. There were fewer places affected by necrosis and inflamatory infiltrates.

The structure of the lobes and radial location of trabeculas in the liver became clearly defined. The cells were less swollen, and their contours became clear-cut. The nuclei feature normal chromic state and the protoplasm of most hepatocytes showed diffused fine granules.

Dystrophic lesion in the myocardium was less pronounced.

The vascular pattern of the iris was more distinct. Inflation and convolution of the vessels decreased, and the blood flow became homogeneous.

Microangiopathy became less pronounced. The thickness of the basal membrane of the muscle capillaries decreased almost one and a half times: in the rats having six months alloxan diabetes said thickness decreased to 65 nm, and that in the rats having alloxan diabets for 12 months decreased to 100-120 nm.

Table 3 contains dta on the variation of the average thickness of the capillary basal membrane of the limb muscles in the rats (in nanometers) at the end of the experiment. For purposes of comparison, the table also contains similar data on the effect produced by the prior art drug, 1,3-dioxo-1H-benz(de)isoquinoline-2(3H)acetic acid (trade-mark "Alrestatin").

The following designations and abbreviations are used in the table: n=the total number of variants treated, i.e. the number of the capillaries examined in the animals of the control and experimental groups; M=arithmetic mean of the variational series-the thickness of the basal membrane of the muscle capillaries, which is a quantitative index of the microangiopathy phase, i.e. gravity of illness; $\delta$=mean square of M deviation; m=mean error; Pk=the level of significance or accuracy in comparison with the control; Pa/groups=- the level of significance or accuracy in each group before and after administering the drugs being tested, $P_{2-3,2-4,3-4}$=the level of significance or accuracy when comparing the the groups 2 and 3, 2 and 4, and 3 and 4.

Thus, the examination results show that the present compound (1,3-dioxo-1H-benz(de)isoquinoline-2(3H)butyric acid) and its sodium and potassium salts are biologically more active than the prior art compound (1,3-dioxo-1H-benz(de)isoquinoline-2(3H)acetic acid) featuring similar properties.

TABLE 3

| Statistical index No. 1 | Control (1) 2 | 1-3-dioxo-1H—benz(de)isoquinoline-2(3H) butyric acid | | Sodium salt | |
|---|---|---|---|---|---|
| | | before administrat. 3 | after administrat. 4 | before administrat. 5 | after administrat. 6 |
| 1. n | 50 | 40 | 40 | 32 | 32 |
| 2. M | 69.8 | 191 | 98.3 | 184 | 102 |
| 3. ±σ | 7.46 | 28 | 11.3 | 22.9 | 14.0 |
| 4. ±m | 2.48 | 3.29 | 1.78 | 4.05 | 2.47 |
| 8. $P_{2-4}$ | | | | | |
| 9. $P_{3-5}$ | | | | | |

| No. | Potassium salt | | 1-3-dioxo-1H—benz(de)isoquinoline2(3H) acetic acid | |
|---|---|---|---|---|
| | before administrat. 8 | after administrat. 9 | before administration 10 | after administration 11 |
| 1. | 36 | 36 | 36 | 36 |
| 2. | 192.5 | 98.6 | 188 | 112 |
| 3. | 27.1 | 9.1 | 22.16 | 12.97 |
| 4. | 4.51 | 1.51 | 3.69 | 2.16 |

Determining the activity of the aldose reductase in the tissues of the experimental animals which were fed 1,3-dioxo-1H-benz(de)isoquinoline-2(3H)butyric acid or its sodium or potassium salts has proven that they feature inhibiting properties with respect to aldose reductase (see Table 4).

TABLE 4

| | Activity of aldose reductase, μmol substruct. per mg of protein | | |
|---|---|---|---|
| Tissue | Normal animal | Animal having alloxan diabetes | Animal having alloxan diabetes + 1,3-dioxo-1H—benz(de)isoquinoline-2(3H) butyric acid |
| Cryst. lens | 1.54 ± 0.23 | 10.3 ± 0.6 | 3.4 ± 0.30 |
| Nerve | 4.19 ± 0.15 | 38.5 ± 4.6 | 25.5 ± 2.1 |
| Aorta | 2.46 ± 0.2 | 16.6 ± 1.1 | 7.4 ± 0.8 |

As may be seen in Table 5 the quantity of sorbitol and fructose in the examined tissues of the experimental animals has decreased.

TABLE 5

| | Sorbitol, μmol per g of tissue | | Fructose, μmol per g of tissue | |
|---|---|---|---|---|
| Tissue | Animals having alloxan diabetes | 1,3-dioxo-1H—benz(de)isoquinoline-2(3H) butyric acid | Animals having alloxan diabetes | 1,3-dioxo-1H—benz(de)isoquinoline-2(3H) butyric acid |
| Cryst. lens | 30 ± 2.4 | 7.18 ± 0.65 | 6.12 ± 1.1 | 2.85 ± 0.56 |
| Nerve | 12.1 ± 1.3 | 9.8 ± 0.94 | 6.25 ± 1.3 | 3.25 ± 0.73 |

The introduction of 1,3-dioxo-1H-benz(de)isoquinoline-2(3H)butyric acid caused changes in the blood indices being examined, which manifested itself in a decrease of the quantity of fructose (2.26±0.16 mg %, p<0.02) and cholesterin (100±7.1 mg %, p<0.005). The level of glucose did not change (340.1±27.8 mg % p<0.5).

Thus, the introduction of 1,3-dioxo-1H-benz(de)isoquinoline-2(3H)butyric acid, or sodium or potassium salts thereof, which are inhibitors of aldose reductase, lead to considerable improvements of the experimental animal biochemical and morphological indices being examined.

The method of producing 1,3-dioxo-1H-benz(de)isoquinoline-2(3H)butyric acid is based on condensation of γ amino butyric acid and the anhydride of 1,8-naphthalic acid in the presence of dimethyl formamide for 40 to 80 minutes at a temperature of 125° to 135° C.

The salts of 1,3-dioxo-1H-benz(de)isoquinoline-2(3H)butyric acid are prepared by reacting 1,3-dioxo-1H-benz(de)isoquinoline-2(3H)butyric acid with a corresponding base.

Given below are examples of how 1,3-dioxo-1H-benz(de)isoquinoline-2(3H)butyric acid and some of its salts, are prepared.

EXAMPLE 1

150 ml of freshly distilled dimethyl formamide, 4.8 g (0.054 mol) of γ-amino butyric acid and 10 g (0.05 mol) of anhydride of the 1,8-naphthalic acid were placed into a retort provided with a thermometer and a reflux condenser. The contents of the retort is were heated and held for 60 minutes, whereafter water was added until the first crystals appeared, and then was allowed to rest until complete crystallization. Recrystallization was effected from ethanol. The yield was 13.03 g (92%). Melting temperature is 178° to 180° C.

C, H, N calculated: 67.84%, 4,6%, 4.95% respectively. Found: 67.84% C, 4.75% H, and 4.90% N.

The infrared spectrum of 1,3-dioxo-1H-benz(de)isoquinoline-2(3H)butyric acid showed intensive absorption bands in the range of 1667 cm$^{-1}$, 1708 cm$^{-1}$ (stretching vibrations C=O); 782 cm$^{-1}$ (deformation vibrations of the C—H naphthalene ring bond), 971 cm$^{-1}$ (vibrations of the isoquinoline ring).

EXAMPLE 2

A mixture was prepared from 98 g of distilled water, 2 g of 1,3-dioxo-1H-benz(de)isoquinoline-2(3H)butyric acid and 0.29 g of caustic soda, which mixture was stirred until all the ingredients were dissolved. The solution thus obtained was filtered and the resulting solution of the sodium salt of 1,3-dioxo-1H-benz(de)isoquinoline-2(3H)butyric acid was administered perorally.

EXAMPLE 3

A mixture was prepared from 98 g of distilled water, 2 g of 1,3-dioxo-1H-benz(de)isoquinoline-2(3H)-butyric acid, and 0.4 g of caustic potash, which mixture was stirred until all the ingredients were dissolved. The thus obtained solution was filtered and the resulting solution of the potassium salt of 1,3-dioxo-1H-benz(de)isoquinoline-2(3H)butyric acid was administered perorally.

While particular embodiments of the invention have been shown and described, various modifications thereof will be apparent to those skilled in the art and therefore it is not intended that the invention be limited to the disclosed embodiments and departures may be made therefrom within the spirit and scope of the invention as defined in the claims.

We claim:

1. 1,3-dioxo-1H-benz(de)isoquinoline-2(3H)butyric acid having the following structural formula

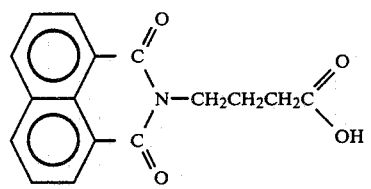

and pharmacologically acceptable salts thereof.

2. A pharmaceutical composition for treating complications arising from diabetes mellitus comprising an effective amount of the compounds of claim 1 in combination with a pharmaceutical carrier.

3. The composition according to claim 2, wherein the amount of said compound is between 0.25 and 0.5 g.

4. The composition according to claim 3, wherein said carrier is a pharmaceutical filler selected from gelatin, talcum, paraffin, starch, lactose, pectin, acetyl cellulose, calcium stearate, magnesium stearate and polyvinylpyrrolidone and said composition is in the form of a tablet.

5. The composition according to claim 2, wherein said compound is:
selected from the group consisting of the sodium salt of 1,3-dioxo-1H-benz(de)isoquinoline-2(3H)butyric acid, or the potassium salt of 1,3-dioxo-1H-benz(de)isoquinoline-2(3H)butyric acid in an amount between 1 and 10 weight % and said carrier is present in an amount of between 90 and 99 weight %.

6. The composition according to claim 3 in the form of an ointment or rectal suppository.

7. The composition according to claim 2, comprising a 1–2% solution of a compound selected from the group consisting of the sodium or potassium salt of 1,3-dioxo-1H-benz(de)isoquinoline-2(3H)butyric acid.

8. A method of treating a warm blooded animal afflicted with complications arising from diabetes mellitus comprising administering the composition of claim 2 to said warm blooded animal.

9. The method of claim 8 wherein the daily dosage is between 50 and 100 mg/kg of body weight.

10. The method of claim 9 further comprising administering said composition perorally in an amount between 50 and 100 mg/kg/day for about thirty days two to three times per year.

* * * * *